(12) United States Patent
Pan et al.

(10) Patent No.: US 10,245,222 B2
(45) Date of Patent: *Apr. 2, 2019

(54) DENTIFRICE COMPRISING ZINC-AMINO ACID COMPLEX

(71) Applicant: Colgate-Palmolive Company, New York, NY (US)

(72) Inventors: Long Pan, Somerset, NJ (US); Shaotang Yuan, East Brunswick, NJ (US); Shira Pilch, Highland Park, NJ (US); James Masters, Ringoes, NJ (US); Zhiqiang Liu, Bridgewater, NJ (US); Vyoma Patel, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/674,557

(22) Filed: Aug. 11, 2017

(65) Prior Publication Data

US 2017/0340539 A1 Nov. 30, 2017

Related U.S. Application Data

(63) Continuation of application No. 14/653,880, filed as application No. PCT/US2012/070513 on Dec. 19, 2012, now Pat. No. 9,763,865.

(51) Int. Cl.
| | |
|---|---|
| A61K 8/44 | (2006.01) |
| A61K 8/20 | (2006.01) |
| A61K 8/04 | (2006.01) |
| A61K 8/27 | (2006.01) |
| A61K 8/73 | (2006.01) |
| A61Q 11/00 | (2006.01) |
| A61K 8/21 | (2006.01) |

(52) U.S. Cl.
CPC .............. *A61K 8/44* (2013.01); *A61K 8/042* (2013.01); *A61K 8/20* (2013.01); *A61K 8/21* (2013.01); *A61K 8/27* (2013.01); *A61K 8/442* (2013.01); *A61K 8/731* (2013.01); *A61Q 11/00* (2013.01); *A61K 2800/58* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 2,503,280 | A | 4/1950 | Lockwood |
| 2,507,088 | A | 5/1950 | Bradley |
| 2,527,686 | A | 10/1950 | Sandberg |
| 2,893,918 | A | 7/1959 | Abramson |
| 3,260,744 | A | 7/1966 | Kenkichi |
| 3,320,174 | A | 5/1967 | Rubinfeld |
| 3,372,188 | A | 3/1968 | Terence |
| 3,535,421 | A | 10/1970 | Briner |
| 3,538,230 | A | 11/1970 | Morton |
| 3,678,154 | A | 7/1972 | Briner |
| 3,741,911 | A | 6/1973 | Shane |
| 3,862,307 | A | 1/1975 | Giulio |
| 3,937,807 | A | 2/1976 | Haefele |
| 3,941,818 | A | 3/1976 | Abdel-Monem |
| 3,959,458 | A | 5/1976 | Agricola et al. |
| 4,039,681 | A | 8/1977 | Abdel-Monem |
| 4,051,234 | A | 9/1977 | Gieske et al. |
| 4,316,824 | A | 2/1982 | Pancheri |
| 4,339,432 | A | 7/1982 | Ritchey et al. |
| 4,340,583 | A | 7/1982 | Wason |
| 4,487,757 | A | 12/1984 | Kiozpeoplou |
| 4,565,693 | A | 1/1986 | Marschner |
| 4,599,152 | A | 7/1986 | Ashmead |
| 4,684,528 | A | 8/1987 | Godfrey |
| 4,687,663 | A | 8/1987 | Schaeffer |
| 4,842,847 | A | 6/1989 | Amjad |
| 4,866,161 | A | 9/1989 | Sikes et al. |
| 4,885,155 | A | 12/1989 | Parran, Jr. et al. |
| 5,004,597 | A | 4/1991 | Majeti et al. |
| 5,061,815 | A | 10/1991 | Leu |
| 5,156,845 | A | 10/1992 | Grodberg |
| 5,188,821 | A | 2/1993 | Gaffar et al. |
| 5,192,531 | A | 3/1993 | Gaffar et al. |
| 5,504,055 | A | 4/1996 | Hsu |
| 5,643,559 | A | 7/1997 | Eigen et al. |
| 5,698,724 | A | 12/1997 | Anderson et al. |
| 5,707,679 | A | 1/1998 | Nelson |
| 5,714,447 | A | 2/1998 | Jones et al. |
| 5,911,978 | A | 6/1999 | Carr et al. |
| 5,993,784 | A | 11/1999 | Hill |
| 6,121,315 | A | 9/2000 | Nair et al. |

(Continued)

FOREIGN PATENT DOCUMENTS

| | | |
|---|---|---|
| CN | 1011729956 A | 10/2007 |
| CN | 101606639 | 12/2009 |

(Continued)

OTHER PUBLICATIONS

Machine Translation of CN101172956A.
Ieva O. Hartwell and John C. Bailar, Jr. JACS 92(5), Mar. 11, 1970, pp. 1284-1289.
Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.
Deschaume et al., "Interactions of aluminum hydrolytic species with biomolecules," New Journal of Chemistry, 2008, 32:1346-1353.
European Food Safety Authority, "Scientific Opinion on the safety and efficacy of tetra-basic zinc chloride for all animal species," EFSA Journal, 2012, 10(5):2672.

(Continued)

*Primary Examiner* — Michael P Cohen

(57) ABSTRACT

Disclosed herein are dentifrices comprising a zinc amino acid halide, which provide a precipitate of zinc oxide upon use with dilution with water and/or saliva. Methods of making and using the dentifrices are also provided.

13 Claims, No Drawings

(56) References Cited

U.S. PATENT DOCUMENTS

| | | | |
|---|---|---|---|
| 6,156,293 A | 12/2000 | Jutila et al. | |
| 6,169,118 B1 | 1/2001 | Bilali | |
| 6,607,711 B2 | 8/2003 | Pedersen | |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 9,572,756 B2* | 2/2017 | Liu | A61K 8/27 |
| 9,675,823 B2* | 6/2017 | Liu | A61K 8/46 |
| 9,757,316 B2* | 9/2017 | Pan | A61K 8/27 |
| 9,763,865 B2* | 9/2017 | Pan | A61K 8/27 |
| 9,775,792 B2* | 10/2017 | Liu | A61K 8/27 |
| 9,913,784 B2* | 3/2018 | Szewczyk | A61K 8/27 |
| 2003/0077332 A1 | 4/2003 | Godfrey | A61K 33/30 424/642 |
| 2004/0042978 A1 | 3/2004 | Embro | |
| 2004/0122088 A1 | 6/2004 | Newsome et al. | |
| 2004/0033916 A1 | 10/2004 | Holerca et al. | |
| 2004/0198998 A1 | 10/2004 | Holerca et al. | |
| 2006/0024252 A1 | 2/2006 | Esposito et al. | |
| 2007/0071698 A1 | 3/2007 | Doss | |
| 2009/0220444 A1 | 9/2009 | Teckenbrock et al. | |
| 2010/0021573 A1 | 1/2010 | Gonzalez et al. | |
| 2010/0266480 A1 | 10/2010 | Huang | |
| 2010/0330163 A1 | 12/2010 | Soparkar | |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |
| 2015/0297500 A1 | 10/2015 | Robinson et al. | |
| 2015/0313813 A1 | 11/2015 | Rege et al. | |
| 2015/0328096 A1 | 11/2015 | Kilpatrick-Liverman et al. | |

FOREIGN PATENT DOCUMENTS

| | | | |
|---|---|---|---|
| CN | 102811698 | 12/2012 | |
| CN | 103156073 | 6/2013 | |
| CN | 103535536 | 1/2014 | |
| DE | 735096 | 5/1943 | |
| EP | 0083486 | 12/1982 | |
| EP | 0108937 | 5/1984 | |
| EP | 0508524 | 10/1992 | |
| EP | 0514553 | 11/1992 | |
| EP | 0740932 A1 | 11/1996 | A61K 8/042 |
| EP | 0842664 | 5/1998 | |
| EP | 1021158 | 7/2000 | |
| EP | 1064946 | 1/2001 | |
| EP | 1203575 | 5/2002 | |
| EP | 1319394 | 6/2003 | |
| EP | 1935395 | 6/2008 | |
| EP | 1529775 | 5/2011 | |
| FR | 2241301 | 3/1975 | |
| GB | 2052978 | 2/1981 | |
| GB | 2109685 | 6/1983 | |
| GB | 2243775 | 11/1991 | |
| JP | S57-158724 | 9/1982 | |
| JP | 2004175790 | 6/2004 | |
| JP | 2009084201 | 4/2009 | |
| JP | 2010132639 | 6/2010 | |
| WO | WO86/00004 | 1/1986 | |
| WO | WO9917735 | 4/1999 | |
| WO | WO199917735 | 4/1999 | |
| WO | WO0169087 | 9/2001 | |
| WO | WO2004054531 | 7/2004 | |
| WO | WO2004/064536 | 8/2004 | |
| WO | WO2007063507 | 6/2007 | |
| WO | WO2011053291 | 5/2011 | |
| WO | WO2011/088199 | 7/2011 | |
| WO | WO2011/123123 | 10/2011 | |
| WO | WO2014/098813 | 6/2014 | |
| WO | WO2014/098814 | 6/2014 | |
| WO | WO2014/098818 | 6/2014 | |
| WO | WO2014/098819 | 6/2014 | |
| WO | WO2014/098821 | 6/2014 | |
| WO | WO2014/098822 | 6/2014 | |
| WO | WO2014/098824 | 6/2014 | |
| WO | WO2014/099164 | 6/2014 | |
| WO | WO2014/099165 | 6/2014 | |
| WO | WO2014/099166 | 6/2014 | |
| WO | WO2014/099167 | 6/2014 | |
| WO | WO2014098825 | 6/2014 | |
| WO | WO2014098826 | 6/2014 | |
| WO | WO2014098828 | 6/2014 | |
| WO | WO2014098829 | 6/2014 | |
| WO | WO2014099039 | 6/2014 | |
| WO | WO2014099226 | 6/2014 | |
| WO | WO2014204439 | 12/2014 | |

OTHER PUBLICATIONS

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 dated Oct. 22, 2013.

International Search Report and Written Opinion for International Application No. PCT/US2012/070492 dated Oct. 22, 2013.

International Search Report and Written Opinion for International Application No. PCT/US2012/070498 dated Sep. 4, 2013.

International Search Report and Written Opinion for International Application No. PCT/US2012/070501 dated Oct. 21, 2013.

International Search Report and Written Opinion for International Application No. PCT/US2012/070505 dated Nov. 20, 2013.

International Search Report and Written Opinion for International Application No. PCT/US2012/070506 dated Oct. 14, 2013.

International Search Report and Written Opinion for International Application No. PCT/US2012/070513 dated Oct. 14, 2013.

International Search Report and Written Opinion for International Application No. PCT/US2012/070521 dated Sep. 30, 2013.

International Search Report and Written Opinion for International Application No. PCT/US2012/070525 dated Sep. 27, 2013.

International Search Report and Written Opinion for International Application No. PCT/US2012/070528 dated Sep. 30, 2013.

International Search Report and Written Opinion for International Application No. PCT/US2012/070534 dated Sep. 26, 2013.

International Search Report and Written Opinion for International Application No. PCT/US2012/070537 dated Oct. 11, 2013.

International Search Report and Written Opinion for International Application No. PCT/US2013/046268 dated Apr. 22, 2014.

International Search Report and Written Opinion for International Application No. PCT/US2013/050845 dated Aug. 13, 2014.

International Search Report and Written Opinion for International Application No. PCT/US2013/068852 dated Nov. 10, 2014.

International Search Report and Written Opinion for International Application No. PCT/US2013/068854 dated Oct. 20, 2014.

International Search Report and Written Opinion for International Application No. PCT/US2013/068859 dated Aug. 4, 2014.

International Search Report and Written Opinion for International Application No. PCT/US2013/068860 dated Oct. 22, 2014.

International Search Report and Written Opinion for International Application No. PCT/US2013/070932 dated Jul. 24, 2014.

International Search Report and Written Opinion for International Application No. PCT/US2014/042947 dated Aug. 22, 2014.

International Search Report and Written Opinion for International Application No. PCT/US2014/042948 dated Aug. 26, 2014.

International Search Report and Written Opinion for International Application No. PCT/US2014/043051 dated Feb. 18, 2015.

Kondrot, "The Importance of Zinc," http://www.healingtheeye.com/Articles/zinc.html, Feb. 21, 2012.

Liang et al., "In vitro scratch assay: a convenient and inexpensive method for analysis of cell migration in vitro," Nature Protocols, 2007, 2(2):329-333.

Liu et al., "The research on zinc coordination number 5 odd structure in zinc complex with L-lysine," J. Molecular Science, 2000, 16(2):114-117, abstract only in English.

Lu et al., "Albumin as a zinc carrier: properties of its high-affinity zinc-binding site". Biochem. Soc. Trans., 2008, 36:1317-1321.

(56) References Cited

OTHER PUBLICATIONS

Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al., Dentin permeability effects of desensitizing dentifrices in vitro. J Periodontol. 1984:55(9):522-525.
Prasad, "Zinc:role in immunity, oxidative stress and chronic inflammation," Current Opinion and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, ε-Zn(OH)2, and simonkolleite, ZnS(OH)8C12H2O, two new minerals from Richelsdorf, Hesse, F.R.G.," B. Jb. Miner. Mh., Apr. 1985, pp. 145-154.
Seil et al., "Antibacterial effect of zinc oxide nanoparticles combined with ultrasound," Nanotechnology,2012, 23:495101.
Soderling et al., "Betaine-cotaining toothpaste relieves subjective symptoms of dry mouth," Acta Odontol. Scand., Apr. 1998, 56(2):65-9.
Stewart et al., "Interdomainzinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42
Zhu et al., "Synthesis and Crystal Structure of [Zn+{H2N(CH2)4CH(NH2)COONa}2SO4−]·H20," Chinese Science Bulletin, Sep. 1990, 35(18):1521-1525.

* cited by examiner

DENTIFRICE COMPRISING ZINC-AMINO ACID COMPLEX

CROSS-REFERENCE TO RELATED APPLICATIONS

This application is Continuation Application filed under 35 U.S.C § 111 of U.S. application Ser. No. 14/653,880, filed on Jun. 19, 2015, which is a United States National Stage Application under 35 U.S.C. § 371 of International Application PCT/US2012/070513, filed on Dec. 19, 2012, the contents of each of which are hereby incorporated by reference in their entireties.

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally saliva has a pH between 7.2 to 7.4. When the pH is lowered and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antibacterial properties in plaque and caries studies.

Soluble zinc salts, such as zinc citrate, have been used in dentifrice compositions, see, e.g., U.S. Pat. No. 6,121,315, but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning. Zinc oxide and insoluble zinc salts, on the other hand, may do a poor job of delivering zinc to the teeth because of their insolubility.

While the prior art discloses the use of various oral compositions for the treatment of dentinal hypersensitivity, dental caries, and enamel erosion and demineralization, there is still a need for additional compositions and methods which provide improved performance in such treatments.

SUMMARY

It has now been discovered that zinc ions can form a soluble complex with an amino acid. The complex comprising zinc and amino acid and optionally an anion and/or oxygen, forms a soluble cationic moiety, which in turn may form a salt with a halide or other anion. When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate that can plug the dentinal tubules, thereby reducing the sensitivity of the teeth. While providing efficient delivery of zinc in comparison to formulations with insoluble zinc salts, the formulations comprising the zinc-amino acid complex do not exhibit the poor taste and mouthfeel, poor fluoride delivery, and poor foaming and cleaning associated with conventional zinc-based oral care products using soluble zinc salts.

In one particular embodiment, the zinc-amino acid complex is a zinc-lysine-HCl complex, for example the novel complex designated ZLC, which may be formed from a mixture of zinc oxide and lysine hydrochloride. ZLC has the chemical structure $[Zn(C_6H_{14}N_2O_2)_2Cl]^+Cl^-$, and may exist in solution of the cationic cation $([Zn(C_6H_{14}N_2O_2)_2Cl]^+)$ and the chloride anion, or may be a solid salt, e.g., a crystal, optionally in mono- or dihydrate form.

The invention thus provides oral care compositions, for example mouthwash, oral gel or dentifrice compositions, that comprise a zinc-amino acid complex, e.g, a zinc-lysine-chloride complex, e.g., ZLC. The compositions may optionally further comprise a fluoride source and or an additional phosphate source. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

In a particular embodiment, the invention provides oral gel compositions, e.g., comprising a zinc-amino acid complex, e.g, a zinc-lysine-chloride complex, e.g., ZLC, which are clear when formulated, but which provide a zinc oxide precipitate when diluted with water.

The invention further provides methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

The invention further provides methods of making the compositions of the invention comprising combining a zinc ion source (e.g., ZnO), an amino acid (e.g., a basic amino acid, e.g., arginine or lysine), and optionally a halide source, for example combining zinc oxide and lysine hydrochloride in aqueous solution, e.g. at a molar ratio of Zn:amino acid of 1:1 to 1:3, e.g., 1:2 and Zn:halide where present of 1:1 to 1:3, e.g., 1:2; optionally isolating the ionic complex thus formed as a solid; and admixing with an oral gel base.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention therefore provides, in a first embodiment, an oral gel composition (Composition 1), comprising zinc in complex with an amino acid; e.g., 1.1. Composition 1 wherein the amino acid is selected from lysine, glycine and arginine, in free or orally acceptable acid addition salt form, e.g., hydrochloride form.
1.2. Composition 1 or 1.1 wherein the amino acid is a basic amino acid, e.g., arginine or lysine, in free or orally acceptable salt form.
1.3. Any of the foregoing compositions further comprising a halide in ionic association with the zinc and amino acid.
1.4. Any of the foregoing compositions wherein the molar ratio of Zn:amino acid is from 3:1 to 1:5, e.g., about 1:2 and the molar ratio of Zn:halide where present is from 3:1 to 1:3, e.g., about 1:2.
1.5. Any of the foregoing compositions wherein the zinc-amino acid complex is formed, in whole or in part, in situ after the composition is applied.
1.6. Any of the foregoing compositions wherein the zinc-amino acid complex is formed, in whole or in part, in situ after the composition is formulated.
1.7. Any of the foregoing compositions, wherein the amino acid is lysine.
1.8. Any of the foregoing compositions, wherein zinc is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight.
1.9. Any of the foregoing compositions, wherein amino acid is present in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.
1.10. Any of the foregoing compositions, wherein a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3
1.11. Any of the foregoing compositions comprising a halide in ionic association with the zinc and amino acid, wherein the halide is selected from the group consisting of fluorine, chlorine, and mixtures thereof.
1.12. Any of the foregoing compositions wherein the zinc amino acid complex is a zinc lysine chloride complex (e.g., $(ZnLys_2Cl)^+Cl^-$ or $(ZnLys_3)^{2+}Cl_2$) or a zinc arginine chloride complex.
1.13. Any of the foregoing compositions wherein the zinc amino acid complex is a zinc lysine chloride complex, e.g., ZLC, e.g., a zinc lysine chloride complex having the chemical structure $[Zn(C_6H_{14}N_2O_2)_2Cl]^+$ $Cl^-$, either in solution of the cationic cation (e.g., $[Zn(C_6H_{14}N_2O_2)_2Cl]^+$) and the chloride anion, or in solid salt form, e.g., crystal form, optionally in mono- or dihydrate form.
1.14. Any of the foregoing compositions in the form of a clear gel which provides a zinc oxide precipitate when diluted.
1.15. Any of the foregoing compositions in the form of a dentifrice, e.g., wherein the zinc-amino acid complex is present in an effective amount, e.g., in an amount of 0.5-4% by weight of zinc, e.g., about 1-3% by weight of zinc, in a dentifrice base.
1.16. Any of the foregoing compositions in the form of a dentifrice, wherein the dentifrice base comprises an abrasive, e.g., an effective amount of a silica abrasive, e.g., 10-30%, e.g., about 20%.
1.17. Any of the foregoing compositions wherein the zinc-amino acid complex is present in an effective amount, e.g., in an amount of 0.1-3% by weight of zinc, e.g., about 0.2-1% by weight of zinc.
1.18. Any of the foregoing compositions further comprising an effective amount of a fluoride ion source, e.g., providing 500 to 3000 ppm fluoride.
1.19. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.20. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.
1.21. Any of the foregoing compositions comprising buffering agents, e.g., sodium phosphate buffer (e.g., sodium phosphate monobasic and disodium phosphate).
1.22. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.
1.23. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.24. Any of the preceding compositions further comprising a viscosity modifying amount of one or more of polysaccharide gums, for example xanthan gum or carrageenan, silica thickener, and combinations thereof.
1.25. Any of the preceding compositions comprising gum strips or fragments.
1.26. Any of the preceding compositions further comprising flavoring, fragrance and/or coloring.
1.27. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
1.28. Any of the foregoing compositions comprising an antibacterially effective amount of triclosan, e.g. 0.1-0.5%, e.g. about 0.3%.
1.29. Any of the preceding compositions further comprising a whitening agent, e.g., a selected from the group consisting of peroxides, metal chlorites, perborates, percarbonates, peroxyacids, hypochlorites, and combinations thereof.
1.30. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
1.31. Any of the preceding compositions further comprising an agent that interferes with or prevents bacterial attachment, e.g., solbrol or chitosan.
1.32. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate
1.33. Any of the preceding compositions further comprising a soluble calcium salt, e.g., selected from calcium sulfate, calcium chloride, calcium nitrate, calcium acetate, calcium lactate, and combinations thereof.
1.34. Any of the preceding compositions further comprising a physiologically or orally acceptable potassium salt, e.g., potassium nitrate or potassium chloride, in an amount effective to reduce dentinal sensitivity.
1.35. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.
1.36. Any of the preceding compositions further comprising a breath freshener, fragrance or flavoring.
1.37. Any of the foregoing compositions, wherein the pH of the composition is approximately neutral, e.g., from pH 6 to pH 8 e.g., about pH 7.
1.38. Any of the foregoing compositions in the form of an oral gel, wherein the amino acid is lysine and the zinc and lysine form a zinc-lysine-chloride complex having the chemical structure $[Zn(C_6H_{14}N_2O_2)_2Cl]^+ Cl^-$, in an amount to provide 0.1-2%, e.g., about 0.5% zinc by weight, and further comprising humectant, e.g., sorbitol, propylene glycol and mixtures thereof, e.g., in an amount of 45-65%, e.g., about 50-60%, thickeners, e.g., cellulose derivatives, e.g., selected from carboxymethyl cellulose (CMC), trimethyl cellulose (TMC) and mixtures thereof, e.g., in an amount of 0.1-2%, sweetener and/or flavorings, and water, e.g., an oral gel comprising

| Ingredients | Wt % |
| --- | --- |
| Sorbitol | 40-60%, e.g., 50-55% |
| ZLC | to provide 0.1-2% Zn, e.g about 0.5% Zn |
| Carboxymethyl cellulose (CMC) and Trimethyl cellulose (TMC) | 0.5-1%, e.g., about 0.7% |
| Flavoring and/or sweetener | 0.01-1% |
| Propylene Glycol | 1-5%, e.g., about 3.00% |

1.1. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The invention further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 1, et seq. to the teeth, and optionally then rinsing with water or aqueous solution sufficient to trigger precipitation of zinc oxide from the composition.

The invention further provides a method of making an oral care composition comprising a zinc amino acid complex, e.g., any of Composition 1, et seq. comprising combining a zinc ion source with an amino acid, in free or salt form (e.g., combining zinc oxide with lysine hydrochloride), in an aqueous medium, optionally isolating the complex thus formed in solid salt form, and combining the complex with an oral care base, e.g., a dentifrice or mouthwash base.

For example, in various embodiments, the invention provides methods to (i) reduce hypersensitivity of the teeth, (ii)

to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The invention further provides Compositions 1, et seq. for use in any of these methods.

The invention further provides the use of zinc and an amino acid to make an oral care composition comprising a zinc amino acid complex.

The invention further provides the use of a zinc amino acid complex, for example a zinc amino acid halide, for example a zinc-lysine-chloride complex, to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

Without intending to be bound by theory, it is believed that the formation of the zinc amino acid halide proceeds via formation of the zinc halide then coordination of amino acid residues around a central zinc. Using reaction of ZnO with lysine hydrochloride in water as an example, the zinc can react with lysine and/or lysine-HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the zinc structure, are possible and contemplated within the scope of the invention. When the complexes are in solid form, they may form crystals, e.g. in hydrated form.

Irrespective of the precise structure of the complex or complexes, however, the interaction of the zinc and the amino acid converts insoluble zinc oxide or zinc salts to a highly soluble complex at approximately neutral pH. With increasing dilution in water, however, the complex disassociates, and the zinc ion converts to insoluble zinc oxide. This dynamic is unexpected—typically ionic compositions become more soluble at higher dilution, not less—and this facilitates deposition of the zinc precipitate on the teeth upon administration, in the presence of saliva and with rinsing. This precipitation occludes the dentinal tubules, thereby reducing hypersensitivity, and also provides zinc to the enamel, which reduces acid erosion, biofilm and plaque formation.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

The actives can be delivered in the form of any oral care formulations, for example a toothpaste, gel, mouthwash, powder, cream, strip, gum, or any other known in the art.

If the actives are delivered in the form of a mouthwash, a person desiring the benefits rinses with the stock solution and natural dilution of the stock solution by saliva will initiate the precipitation of the zinc. Alternatively, the person can mix the stock solution with appropriate amount of an aqueous diluent (such as approximately 1 part stock solution and 8 parts water for the zinc-lysine samples), and rinse with the mixture.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel.

In another embodiment, the stock solution, or a mixture of stock solution with water, is applied to the teeth in a gel formulation, e.g., wherein the gel can stay on the tooth for an extended period of time for effective treatment.

In another embodiment, the active is provided in a toothpaste. Upon brushing, the active is diluted by saliva and water, leading to precipitation and the formation of deposits and occluding particles.

The rate of precipitation from the formulation can be modulated by adjusting concentration of the complex in the stock solution, and changing the ratio of the stock to water. A more diluted formula leads to faster precipitation and is thus preferred when a fast treatment is desired.

The benefits of the oral care compositions of the invention are numerous. By providing zinc ions and zinc containing compounds that can release zinc ions in oral cavities, the oral care compositions of the invention provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine. These amino acids provide multiple benefits. For example, basic amino acids lead to higher pH of the plaque and can provide anticaries benefits. In addition, it is also expected that arginine can enhance the activity of arginolytic bacteria, leading to a more healthy plaque. Arginine is also known to promote wound healing and collagen integrity.

The composition can include the zinc amino acid halide and/or precursors thereof. Precursors, which can react in situ with water to form the zinc amino acid halide, include (i) zinc and an amino acid hydrohalide, or (ii) zinc chloride and amino acid, or (iii) a zinc ion source, an amino acid, and a halogen acid, or (iv) combinations of (i), (ii), and/or (iii). In one embodiment, the zinc amino acid halide can be prepared at room temperature by mixing the precursors in a solution, such as water. The in situ formation provides ease of formulation. The precursors can be used instead of first having to form the zinc amino acid halide. In another embodiment, the water permitting formation of the zinc amino acid halide from the precursor comes from saliva and/or rinsing water that comes into contact with the composition after application.

The zinc amino acid halide is a water soluble complex formed from the halide acid addition salt of zinc (e.g., zinc chloride) and an amino acid, or from the halide acid addition salt of an amino acid (e.g., lysine hydrochloride) and zinc ion source, and/or from combination of all three of a halogen acid, an amino acid, and a zinc ion source.

Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments the amino acid is a neutral or acidic amino acid, e.g., glycine.

As seen from the examples below, the precipitation of zinc from the complex upon dilution with water is most notable when the complex is formed from a basic amino acid. Thus, where precipitation upon dilution is desired, a basic amino acid may be preferred. In some embodiments, therefore, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine.

The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

The zinc ion source for combination with an amino acid halide or an amino acid optionally plus halogen acid in this case may be, e.g., zinc oxide or zinc chloride.

In certain embodiments, the amount of zinc amino acid halide in the composition is 0.05 to 10% by weight of the composition. In certain embodiments, precursors, e.g., zinc and amino acid hydrohalide, are present in amounts such that when combined into the zinc amino acid halide, the zinc amino acid halide would be present in an amount of 0.05 to 10% by weight of the composition. In either of these embodiments, the amount of the zinc amino acid halide can be varied for the desired purpose, such as a dentifrice or a mouthwash. In other embodiments, the amount of the zinc amino acid halide is at least 0.1, at least 0.2, at least 0.3, at least 0.4, at least 0.5, at least 1, at least 2, at least 3, or at least 4 up to 10% by weight of the composition. In other embodiments, the amount of the zinc amino acid halide is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, zinc is present in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, amino acid hydrohalide is present in an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

Where precursor materials are present, they are preferably present in molar ratios approximately as required to produce the desired zinc amino acid halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, a molar ratio of zinc to amino acid is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., TBZC and amino acid hydrohalide, will not significantly react to form the zinc amino acid halide. When contacted with a sufficient amount of water, which can be in the form of saliva and/or water used to rinse the mouth during or after application of the composition, the precursors will then react to form the zinc amino acid halide, then upon further dilution, will provide the zinc-containing precipitate to the teeth.

The carrier represents all other materials in the composition other than the zinc amino acid halide complex or its precursors. The amount of carrier is then the amount to reach 100% by adding to the weight of the zinc amino acid halide, including any precursors.

Active Agents:

The compositions of the invention may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Amino Acids:

In some embodiments, the compositions of the invention comprise an amino acid. In particular embodiments, the amino acid may be a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine. In certain embodiments, the basic amino acid is arginine, for example, l-arginine, or a salt thereof.

In various embodiments, the amino acid is present in an amount of about 0.5 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % of the total composition weight in the case of a dentifrice, or for example about 0.5-2 wt. %, e.g., about 1% in the case of a mouthwash.

Abrasives:

The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar Control Agents:

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers:

The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

The general reaction for formation of ZLC is as follows:

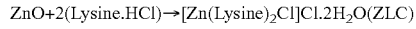

A 2:1 molar ratio of ZnO:Lysine.HCl suspension is prepared with stirring at room temperature for about 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. The dimension of this complex molecule is 1.7 nm*7.8 nm*4.3 nm. In this complex, Zn cation is coordinated by two lysine ligands with two N atoms from $NH_2$ groups and O atoms from carboxylic groups in an equatorial plane. It displays a distorted square-pyramidal geometry with the apical position occupied by a Cl atom. This novel structure gives rise to a positive cation moiety, to which a Cl anion is combined to form an ionic salt.

Laboratory Scale-Up Synthesis of Pure ZLC Powder:

2 mole of LysineHCl is dissolved in 1000 ml DI water with stirring at room temperature, 1 mole of solid ZnO is added slowly to the LysineHCl solution with stirring and the stirring is continued at RT overnight (about 12 hours). The suspension solution is centrifuged at high speed for 15 mins. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained. PXRD confirms the purity of ZLC powder compared to ZLC crystal.

Example 2

Four 500 g mouthwash batches which contain NaF, ZLC, $ZnCl_2$ and ZnO as active ingredient are formulated with the ingredients shown in Table 1. The objective of this study is to compare the clarity of samples with different actives. Turbidity is evaluated by the percent transmission of light through the solution as measured by a TurbiScan® dispersion stability analyzer. The higher the percent transmission, the more transparent the. Thus, a smaller percent transmission suggests that the solution is more turbid. The concentration of zinc ions in ZLC solution is 25300 ppm obtained by ICP (Inductively Coupled Plasma) analysis, which corresponds to approximately 17% weight of ZLC actives in the solution. Zinc ion concentration in all batches is controlled to same level, i.e., 1.01 wt %. Among the four batches, the one that has ZnO as active appears milk white, with 0% transmission, while the other three samples are as clear as the deionized water (Table 2).

TABLE 1

| Ingredients | % | Loading (g) | Actual (g) |
|---|---|---|---|
| Mouthwash with NaF | | | |
| Sorbitol 70% sol | 5.5 | 27.5 | 27.51 |
| Sodium Fluoride | 0.05 | 0.25 | 0.25 |
| Na Saccharin | 0.02 | 0.1 | 0.1 |
| Propylene Glycol | 7 | 35 | 35 |
| Poloxomer 407 | 0.4 | 2 | 2.01 |
| Citric Acid | 0.02 | 0.1 | 0.1 |
| Potassium Sorbitol | 0.05 | 0.25 | 0.25 |
| Glycerin | 7.5 | 37.5 | 37.5 |
| Peppermint Flavor | 0.1 | 0.5 | 0.5 |
| Deionized water | 79.36 | 396.8 | 396.8 |
| Total | 100 | 500 | 500.02 |
| Mouthwash with $ZnCl_2$ | | | |
| Sorbitol 70% sol | 5.5 | 27.5 | 27.5 |
| ZnCl2 47.97% Zn | 2.11 | 10.55 | 10.56 |
| Na Saccharin | 0.02 | 0.1 | 0.1 |
| Propylene Glycol | 7 | 35 | 34.98 |
| Poloxomer 407 | 0.4 | 2 | 2 |
| Citric Acid | 0.02 | 0.1 | 0.1 |
| Potassium Sorbitol | 0.05 | 0.25 | 0.25 |
| Glycerin | 7.5 | 37.5 | 37.48 |
| Peppermint Flavor | 0.1 | 0.5 | 0.48 |
| Deionized water | 77.3 | 386.5 | 386.88 |
| Total | 100 | 500 | 500.33 |
| Zn % | 1.01 | | |
| Mouthwash with ZnO | | | |
| Sorbitol 70% sol | 5.50 | 27.5 | 27.55 |
| ZnO 80.34% Zn | 1.26 | 6.3 | 6.28 |

TABLE 1-continued

| Ingredients | % | Loading (g) | Actual (g) |
|---|---|---|---|
| Na Saccharin | 0.02 | 0.1 | 0.1 |
| Propylene Glycol | 7 | 35 | 34.98 |
| Poloxomer 407 | 0.4 | 2 | 2.02 |
| Citric Acid | 0.02 | 0.1 | 0.1 |
| Potassium Sorbitol | 0.05 | 0.25 | 0.25 |
| Glycerin | 7.5 | 37.5 | 37.52 |
| Peppermint Flavor | 0.1 | 0.5 | 0.52 |
| Deionized water | 78.15 | 390.75 | 390.62 |
| Total | 100 | 500 | 499.94 |
| Zn % | | 1.01 | |
| Mouthwash with ZLC | | | |
| Sorbitol 70% sol | 5.5 | 27.5 | 27.49 |
| ZLC 2.53% Zn | 40 | 200 | 200 |
| Na Saccharin | 0.02 | 0.1 | 0.1 |
| Proylene Glycol | 7 | 35 | 35.01 |
| Poloxomer 407 | 0.4 | 2 | 2 |
| Citric Acid | 0.02 | 0.1 | 0.1 |
| Potassium Sorbitol | 0.05 | 0.25 | 0.25 |
| Glycerin | 7.5 | 37.5 | 37.5 |
| Peppermint Flavor | 0.1 | 0.5 | 0.5 |
| Deionized water | 39.41 | 197.05 | 196.98 |
| Total | 100 | 500 | 499.93 |
| Zn % | | 1.01 | |

TABLE 2

| | DI water | NaF MW | ZLC MW | $ZnCl_2$ MW | ZnO MW |
|---|---|---|---|---|---|
| pH | 5.89 | 4.79 | 7.18 | 3.49 | 7.03 |
| Turbidity (% Transmission) | 88.68% | 88.40% | 86.23% | 89.03% | 0.0016% |

Dilution Experiment:

All original mouthwash batches are diluted into 2 fold, 4 fold, 8 fold, 16 fold and 32 fold. Turbidity measurements are performed after all solutions are prepared and well shaken. The turbidity data of the samples are shown in Table 3, 4, 5 and 6, for the dilutions of mouthwash containing NaF, ZLC, $ZnCl_2$ and ZnO respectively. Precipitation is observed as ZLC mouthwash sample is diluted, but the turbidity of the other samples is unchanged.

TABLE 3

| | 2X | 4X | 8X | 16X | 32X |
|---|---|---|---|---|---|
| Turbidity (% transmission) | 89.85% | 88.90% | 88.44% | 88.77% | 88.61% |

TABLE 4

| | 2X | 4X | 8X | 16X | 32X |
|---|---|---|---|---|---|
| pH | 7.46 | 7.67 | 7.86 | 7.80 | 7.94 |
| Turbidity (% transmission) | 86.73% | 85.99% | 60.50% | 59.61% | 23.21% |

TABLE 5

| | 2X | 4X | 8X | 16X | 32X |
|---|---|---|---|---|---|
| Turbidity (% transmission) | 88.63% | 88.04% | 87.77% | 87.42% | 87.99% |

TABLE 6

| | 2X | 4X | 8X | 16X | 32X |
|---|---|---|---|---|---|
| Turbidity (% transmission) | 0% | 0% | 0% | 0% | 0% |

Aging Experiment:

The diluted ZLC mouthwash samples are placed in a 37° C. oven over the weekend (about 60 hours) for a stability study. Results are shown in Table 7. Precipitation can be observed started from 4 fold dilution. The largest amount of precipitation is found at 16 fold dilution. The original batch, however, is still stable and does not show precipitation even being aged for 60 hours.

TABLE 7

| | 0X | 2X | 4X | 8X | 16X | 32X |
|---|---|---|---|---|---|---|
| pH | 7.16 | 7.48 | 7.65 | 7.82 | 7.85 | 7.95 |
| Turbidity (% transmission) | 86.16% | 86.15% | 8.33% | 6.37% | 0.14% | 9.91% |

Compared with the mouthwash batches formulated using $ZnCl_2$ and ZnO, only the formulation with ZLC as active can form a clear, stable solution but generate the precipitate when diluted. This ZLC mouthwash formulation has a neutral pH and is stable at 37° C. The ZLC provides a mouthwash formulation which is stable on the shelf but precipitates at dilute solution. This formation of insoluble precipitate by dilution allows formation of "plugs" in dentine tubules, providing benefits for hypersensitivity.

Example 3

The mouthwash formulation of the preceding example using ZLC as active ingredient not only shows competitive clarity with current commercial mouthwash product which contains NaF as active ingredient, but also exhibits precipitation ability when diluted by water. This unique property facilitates anti-sensitive and anti-cavity effects, and it is thus of interest to employ ZLC in a toothpaste product.

An oral gel toothpaste with ZLC as active ingredient is formulated and compared to other formulations containing $ZnCl_2$, ZnO, and NaF. Only the ZLC formulation shows competitive clarity as current gel phase containing NaF. The precipitation property of ZLC gel phase is also investigated by hydrolysis reaction study, providing evidence that when the teeth are being brushed with toothpaste containing ZLC, the insoluble particles formed during brushing can penetrate into the dentin tubules and block the tubules resulting to anti-sensitive effect and signal for the consumer.

Four 500.0 g gel phase batches which contain NaF (control), ZLC, $ZnCl_2$ and ZnO as active ingredient are formulated with the ingredients shown in Table 8. The clarity of samples with different actives is compared, and the precipitation characteristic of ZLC gel phase by dilution is evaluated. The concentration of zinc ions in ZLC solution is 25300 ppm obtained by ICP, which in terms gives approximately 17% weight of ZLC actives in the solution. Zinc ion concentration in the following batches are all prepared at 0.5% (w/w) zinc level.

TABLE 8

| Ingredients | % | Loading (g) | Actual (g) |
|---|---|---|---|
| Oral gel with ZLC (2.53% Zn) | | | |
| Sorbitol 70% sol | 76.03 | 380.15 | 380.14 |
| ZLC aqueous solution 2.53% Zn | 20 | 100 | 100 |
| Carboxymethyl cellulose (CMC) and Trimethyl cellulose (TMC) | 0.7 | 3.5 | 3.51 |
| Na Saccharin | 0.27 | 1.35 | 1.35 |
| Propylene Glycol | 3 | 15 | 15 |
| Total | 100 | 500 | 500 |
| % Zn | | 0.506 | 0.5060% |
| Oral gel with ZnCl$_2$ (47.97% Zn) | | | |
| Sorbitol 70% sol | 80 | 400 | 399.99 |
| ZnCl2 47.97% Zn | 1.06 | 5.275 | 5.27 |
| CMC TMC | 0.7 | 3.5 | 3.5 |
| Na Saccharin | 0.27 | 1.35 | 1.35 |
| Propylene Glycol | 3 | 15 | 14.98 |
| DI water | 14.98 | 74.875 | 74.91 |
| Total | 100 | 500 | 500 |
| % Zn | | 0.508 | 0.5056% |
| Oral gel with ZnO (80.34% Zn) | | | |
| Sorbitol 70% sol | 80.2 | 401 | 400.99 |
| ZnO 80.34% Zn | 0.63 | 3.15 | 3.15 |
| CMC TMC | 0.7 | 3.5 | 3.5 |
| Na Saccharin | 0.27 | 1.35 | 1.35 |
| Propylene Glycol | 3 | 15 | 15 |
| DI water | 15.2 | 76 | 75.99 |
| Total | 100 | 500 | 499.98 |
| % Zn | | 0.505 | 0.5062% |
| Oral gel with NaF | | | |
| Sorbitol 70% sol | 80.2 | 401 | 401 |
| NaF | 0.76 | 3.8 | 3.79 |
| CMC TMC | 0.7 | 3.5 | 3.51 |
| Na Saccharin | 0.27 | 1.35 | 1.35 |
| Propylene Glycol | 3 | 15 | 15.01 |
| DI water | 15.07 | 75.35 | 75.36 |
| Total | 100 | 500 | 500.02 |

Lambda 25 UV/VIS Spectrometer (PerkinElmer) is used to obtain absorbance information for all samples in order to compare the clarity of gel phase between different actives. Absorbance is a logarithmic measure of the amount of light that is absorbed when passing through a substance. Since the particles in the gel absorb light, the more particles existing in solution, the more light absorbed by the gel. Thus, a small number of absorbance of a gel indicates a higher clarity. The absorbance is corrected by using deionized (DI) water as the blank solution under the light source wavelength of 610 nm. ZnO is not dissolved and is suspended in gel phase resulting a high absorbance. Even though ZnCl$_2$ is soluble in water, the gel phase containing ZnCl$_2$ appears cloudy. Only the gel phase formulated by ZLC forms a homogenous solution and shows competitive clarity as the gel phase formulated by NaF. The absorbance and pH of all samples are shown in Table 9.

TABLE 9

| | NaF | ZLC | ZnCl$_2$ | ZnO |
|---|---|---|---|---|
| Absorbance | 0.0344 | 0.1765 | 0.9204 | 2.4626 |
| pH | 7.63 | 7.37 | 5.25 | 8.30 |

Dilution Experiment:

All original gel phase batch are diluted into 2 fold, 4 fold, 8 fold, 16 fold and 32 fold. There is a decrease of absorbance as the NaF gel, ZnCl$_2$ gel, and ZnO gel are further diluted, and an increase of absorbance in the further diluted ZLC gel solution. This observation confirms the formation of precipitate when ZLC gel is being diluted by water. The pHs of 2 fold, 4 fold, 8 fold, 16 fold, and 32 fold diluted ZLC gel solution are 7.71, 7.91, 8.03, 8.12, and 8.14, respectively.

TABLE 10

| Active Ingredient | 2 fold dilution | 4 fold dilution | 8 fold dilution | 16 fold dilution | 32 fold dilution |
|---|---|---|---|---|---|
| NaF | 0.0106 | 0.0104 | 0.0107 | 0.0075 | 0.0137 |
| ZLC | 0.1436 | 0.1887 | 0.1860 | 0.1336 | 0.2998 |
| ZnCl$_2$ | 0.7315 | 0.3700 | 0.1701 | 0.0570 | 0.0280 |
| ZnO | 2.4630 | 2.5340 | 2.1883 | 1.8638 | 1.0492 |

The above gels can be used alone or in a toothpaste having a gel phase and an abrasive paste phase. ZLC as active ingredient in gel phase of toothpaste formulation. Compared with the gel phase batches formulated by ZnCl$_2$ and ZnO, only the formulation with ZLC as active shows competitive clarity and pH as the one used in commercial product (NaF as active ingredient). The dilution experiment shows that only ZLC gel phase can form insoluble precipitate from transparent gel when it is diluted. The formation of insoluble precipitate by dilution facilitates the formation of "plugs" in dentine tubules after using this type of toothpaste, and moreover, it provides a white precipitate signal during consumer use.

Example 4

Dentinal occlusion by an oral gel with ZLC is measured compared to an oral gel without ZLC for potential anti-hypersensitivity benefit. A Flodec instrument is used to measure fluid flow through dentin tubules. A Pashley cell method (e.g., Pashley D H, O'Meara J A, Kepler E E, et al. Dentin permeability effects of desensitizing dentifrices in vitro. *J Periodontol.* 1984; 55(9):522-525) is used following a procedure used to measure dentinal occlusion on mouth wash formulations by S. Mello. Two 10 minute treatments of 400 μl sample are applied with a pipette on dentin disks at 10 minute intervals. After each treatment the disks are rinsed with phosphate buffered saline (PBS) and measured for flow using a FLODEC apparatus, a device which tracks the position of a meniscus inside a capillary tube to measure small changes in volume. Table 8 shows average flow of the oral gel with ZLC and percent flow reduction after sample application.

TABLE 11

| Average Flow (μl/min) of Oral Gel with ZLC | | | | % Flow Reduction |
|---|---|---|---|---|
| | Baseline | Treatment#2 | Difference | (from Baseline) |
| Rep#1 | 7.51 | 3.47 | 4.05 | 53.87 |
| Rep#2 | 13.02 | 7.20 | 5.82 | 44.68 |
| Rep#3 | 25.74 | 19.79 | 5.95 | 23.13 |
| AVG | | | | 40.56 |
| STDEV | | | | 15.78 |

As shown above, the average percent flow reduction of oral gel with ZLC triplicates is about 41% through dentin tubules.

Table 12 shows average flow of oral gel without ZLC (control) and percent flow reduction after sample application.

TABLE 12

| | Average Flow (μl/min) of Oral Gel without ZLC (Control) | | | % Flow Reduction |
|---|---|---|---|---|
| | Baseline | Treatment#2 | Difference | (from Baseline) |
| Rep#1 | 7.25 | 5.02 | 2.23 | 30.85 |
| Rep#2 | 13.94 | 8.43 | 5.51 | 39.57 |
| Rep#3 | 22.84 | 17.93 | 4.91 | 21.53 |
| AVG | | | | 30.65 |
| STDEV | | | | 9.02 |

As shown above, the average percent flow reduction of oral gel without ZLC triplicates (control) is about 31% through dentin tubules.

The oral gel with ZLC shows directionally better performance, as compared to the oral gel without ZLC (control) in an in-vitro hydraulic conductance model using a FLODEC apparatus.

Example 5

Various dilutions of ZLC are prepared to evaluate its efficiency in producing visible precipitates and/or flocculation, which can be delivered in situ onto an oral surface or into a dental opening, such as open tubules.

A neat solution of ZLC is prepared by 1), reacting 0.5 mole of ZnO powder with 1 mole of lysine HCl in 1 liter of water at room temperature for about 2 hours, and 2) collecting the supernatant through centrifugation followed by filtration using a 0.45 micron membrane. The neat solution has a zinc concentration of 2.39% by weight, and a pH of about 7.03.

Dilution experiment is conducted by mixing the neat solution with deionized water. The neat solution is diluted by 2×, 4×, 6×, 7×, 8×, 10×, 12×, 16×, 20×, 24×, 28×, and 32×, corresponding to initial zinc concentrations of 1.20%, 0.598%, 0.398%, 0.341%, 0.299%, 0.239%, 0.199%, 0.149%, 0.120%, 0.0996%, 0.0854%, 0.0747%, by weight, respectively. The diluted samples are kept at 37° C., and the rates at which flocculation/precipitation occurred are monitored. Dilutions with initial zinc concentrations at 0.149% and 0.199% are able to generate some visible flocculation within 30 minutes from the time point when the stock solution is mixed with water. One hour from mixing, visible flocculation are observed in dilutions with initial zinc concentrations of between 0.0854% and 0.239%. One and a half hours after mixing, visible flocculation are observed in dilutions with initial zinc concentrations of between 0.0747% and 0.2390/%. Two hours after mixing, the additional sample with initial zinc concentration of 0.299/also showed presence of flocculation. After a total of 19 hours, flocculation and/or precipitation can be observed in all samples except the one with initial zinc concentration of 1.20%, and the ones with initial zinc concentrations of between 0.0747% and 0.239% exhibit the most precipitates.

pH values of final diluted samples are suitable for oral care applications. The samples with initial zinc concentrations of 0.0747%, 0.0854%, 0.0996%, 0.120%, 0.149%, 0.199 wt % and 0.239% had a final pH value of 7.99, 8.13, 8.11, 7.97, 7.99, 6.80, and 6.70, respectively. These pH values were well within the range of 5.5 to 10, which defines the suitable range for oral care formulations.

Zinc is present in the precipitates primarily in the form of zinc oxide. Lysine is present in the precipitate as an integral component thereof and/or as an impurity.

Example 6

Confocal images demonstrate the efficiency of ZLC in generating surface deposits and occluding tubule openings on dentine surface, under conditions where visible precipitation can be formed.

The deposition/occlusion assay is conducted using human dentine slices and the neat solution of Example 5. The dentine slices were prepared by cutting human tooth into thin dentine sections of about 800 microns in thickness, choosing a test side, sanding said test side using a sandpaper of about 600 grit, polishing said test side using a Buehler polishing cloth and 5 micron Buehler aluminum oxide, acid-etching said dentine section in 1% (by weight) citric acid solution for about 20 seconds, sonicating said dentine section for 10 minutes, and storing said dentine section in phosphate buffered saline (PBS, pH 7.4).

For treatment, the neat solution is diluted 16-fold with water, yielding a treatment solution with initial zinc concentration of about 0.149% by weight. The dentine section is immersed in the treatment solution for 1 hour at 37° C. The treated dentine section is then removed from the treatment solution, and rinsed 4 times, each time with 1 mL of PBS. The dentine section is then dried using a paper-based tissue and examined under confocal microscope in both XYZ and XYZ modes. Subsequent treatments are conducted in the same manner.

Progressive deposition and occlusion can be observed via confocal imaging. The first treatment leads to noticeable deposition. The second treatment leads to complete surface coverage, including blocking of substantially all tubule openings. The surface deposits can be 10 microns or more in thickness. After the third treatment, complete surface coverage and complete blocking of tubule openings are observed. The surface deposits can be 25 microns or more in thickness. The deposits impart a white color to the dentine surface.

The surface deposits provide various benefits, including those commonly associated with zinc and lysine, as well as protection from erosion through the neutralization of erosive acids by the deposits, protection from sensitivity through the blocking of tubules, and controlled release of actives due to the gradual release of zinc and lysine from the deposits, particularly upon acid challenge.

Example 7

Confocal images demonstrate the efficiency of ZLC in generating a surface deposits and occluding tubule openings on dentine surface, under conditions where visible precipitation is not observed.

Dentine sections, as prepared in Example 6, are repeatedly treated with ZLC dilutions with initial zinc concentration of 0.0747% by weight. Each treatment involved 32 mL of diluted solution (1 mL of neat solution from Example 5 and 31 mL of deionized water) and lasts for 10 minutes at 37° C., during which time, no precipitation is observed by naked eyes. The dentine section is examined under the confocal microscope after each treatment. After 4 consecutive treatments, significant surface deposition is observed. After 12 consecutive treatments, complete surface coverage is observed leaving no sign of presence of tubule openings.

Therefore, surface deposition and tubule occlusion can occur under conditions, both in terms of dilution ratios and treatment durations, that do not produce visible precipitation.

Example 8

Test dentifrice comprising zinc-lysine, 1450 ppm fluoride, and phosphates is prepared as described in Table 13 (below).

TABLE 13

| Ingredient | Wt % |
| --- | --- |
| PEG600 | 3 |
| CMC-7 | 0.65 |
| Xanthan | 0.2 |
| Sorbitol | 27 |
| Glycerin | 20 |
| Saccharin | 0.3 |
| Tetrasodium pyrophosphate | 0.5 |
| Calcium pyrophosphate | 0.25 |
| Sodium phosphate dibasic | 3.5 |
| Sodium fluoride (to provide 1450 ppm fluoride) | 0.32 |
| Titanium dioxide | 0.5 |
| Abrasive silica | 8 |
| Thickener silica | 8 |
| ZLC | 7 |
| Sodium lauryl sulfate | 1.5 |
| Flavoring | 1.2 |
| Water | QS |

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A dentifrice comprising a zinc-amino acid-halide complex, wherein the amino acid is lysine, and complex is a zinc lysine chloride complex having the chemical structure [Zn(C$_6$H$_{14}$N$_2$O$_2$)$_2$Cl]$^+$Cl$^-$, either in solution of the cation [Zn(C$_6$H$_{14}$N$_2$O$_2$)$_2$Cl]$^+$ and the chloride anion, or in solid salt form, optionally in mono- or dihydrate form.

2. The dentifrice of claim 1, wherein the zinc-amino acid-halide complex is formed from precursors.

3. The dentifrice of claim 2, wherein the precursors are a zinc ion source, an amino acid source, and a halide source.

4. The dentifrice of claim 3, wherein the halide source is part of the zinc ion source, the amino acid source, or a halogen acid.

5. The dentifrice of claim 1, wherein the amount of zinc is 0.05-4% by weight of the composition.

6. The dentifrice of claim 1, wherein the zinc ion source and amino acid source form the complex, in situ after the composition is applied.

7. The dentifrice of claim 1, wherein the zinc is solubilized, such that the dentifrice is substantially clear, which provides a zinc precipitate upon use and dilution with saliva and/or rinsing.

8. The dentifrice of claim 1, further comprising an effective amount of a fluoride ion source.

9. The dentifrice of claim 1, further comprising an orally acceptable base comprising ingredients selected from one or more of: abrasives, buffering agents, humectants, surfactants, thickeners, gum strips or fragments, breath fresheners, flavoring, fragrance, coloring, antibacterial agents, whitening agents, agents that interfere with or prevent bacterial attachment, calcium sources, phosphate sources, orally acceptable potassium salts, and anionic polymers.

10. The dentifrice of claim 1, wherein the pH of the dentifrice is from pH 6 to pH 8.

11. The dentifrice of claim 1, wherein the dentifrice is a substantially clear gel.

12. A method of manufacturing a dentifrice according to claim 1, comprising the step of adding a zinc ion source together with an amino acid in complex during manufacture.

13. A method of treating or reducing dental enamel erosion cleaning the teeth, reducing bacterially-generated biofilm and plaque, reducing gingivitis, inhibiting tooth decay and formation of cavities, and/or reducing dentinal hypersensitivity comprising applying a dentifrice according to claim 1 to the teeth, and, optionally, then rinsing with water or aqueous solution sufficient to trigger precipitation of zinc oxide from the gel.

* * * * *